USOO6100456A

United States Patent [19]
Sticklen et al.

[11] Patent Number: 6,100,456
[45] Date of Patent: Aug. 8, 2000

[54] LEPIDOPTERAN INSECT RESISTANT TRANSGENIC POTATO PLANTS

[75] Inventors: Masomeh B. Sticklen, Okemos, Mich.; Jianping Cheng, Blacksburg, Va.

[73] Assignee: Board of Trustees operating Michigan State University, East Lansing, Mich.

[21] Appl. No.: 07/851,509

[22] Filed: Mar. 16, 1992

[51] Int. Cl.$^7$ .............................. A01H 5/00; C12N 15/82
[52] U.S. Cl. ........................................ 800/317.2; 800/279
[58] Field of Search ............................ 800/205, DIG. 42, 800/279, 302, 317.2; 536/23.71; 435/172.3, 240.4, 320.1, 69.1, 419, 468, 469; 935/67

[56] References Cited

U.S. PATENT DOCUMENTS

| | | | |
|---|---|---|---|
| 4,695,455 | 9/1987 | Barnes et al. | 435/172.3 |
| 5,010,001 | 4/1991 | Pollock | 435/69.1 |

OTHER PUBLICATIONS

Hofte, H., et al., Microbiol. Reviews, 53, 242–255 (1989).
Dulmage, H.T., Microbial of Control of Pest & Plant Diseases 1970–1980 in : H.D. Burges (ed), Academic, London, pp. 193–222 (1980).
Bulla, L.A., et al., Biochem. Bio Phys. Res. Commun. 91, 1123–1130 (1979).
Adang, M.J., et al., Gene, 36, 289–300 (1985).
Beegle, C.C., et al., Environ. Entomol., 10, 400–401 (1981).
Perlak, F.J., et al., Bio./Technology 8, 939–943 (1990).
Barton. K.A., et al., Plant Physiol. 85, 1103–1109 (1987).
Vaeck, M., et al., Nature, 328, 33–37 (1987).
Delannay, X., et al., Bio/Technology, 7, 1265–1269 (1989).
MacIntosh, S., et al., J. Invertebrate Pathology 56, 258–266 (1990).
Atwater, JA., et al., Regulated mRNA stability Annu. Rev. Genet. 24: 519–541 (1990).
Barnes, W.M., Variable patterns of expression of luciferase in transgenic tobacco leaves. Proc. Natl. Acad. Sci. US, v. 87 9183–9187 (1990).
Wenzler, H., et al., Plant Science, 63, 79–85 (1989).
Lee, J.S., et al., Molecular characterization & phylogenetic studies of a woundinducible proteinase inhibitor I gene in Lycopersicon species Proc. Natl. Acad. Sci. USA V. 83, 7277–7281 (1986).
Ditta, G., et al., Plasmid, 13, 149–153 (1985).
Murashige, T., et al., Physiol Plant., 15, 473–497 (1962).
Horsch, R.B., et al., Plant Molecular Biology Manual, Kluwer Academic Publishers, Dordrecht, pp. A5: 1–9 (1989).
Southern, E.M., J. Mol. Biol. 98, 503–517 (1975).
Sambrook, J., et al., Molecular Cloning: A Laboratory Manual, 2nd ed., Cold Spring Harbor Laboratory Press, Cold Spring Harbor (1988).
Feinberg, A.P., et al., Annu. Biochem. 132, 6–13 (1983).
Rogers, S.O., et al., Extraction of DNA from plant tissues, in: Gelvin (eds), Plant Molecular Biology Manual, Kluwer Academic Publishers, Dordrecht, pp. A6: 1–10 (1988).
Gilmour, S.J., et al., Plant Physiol, 87, 745–750 (1988).
Wrewchner, D.H., et al., Nucl. Acids Res. 12, 1349–1359 (1984).
Wilkinson, L., SYSTAT: the System for statistics, SYSTAT, Inc., Prints, Evenston, IL.p.190–316 (1990).
Peferoen, et al. in "The Molecular and Cellular Biology of Potato" (Vayla and Park, eds.) vol. 3, pp. 193–204, Wallingford, Oxon, UK, 1991. OCLC Copyright Sep. 19, 1990 by UKM Lib.
Perlak, et al (Oct. 1990) Bio/Technology 8: 939–943.
Wenzler, et al. (1989) Plant Science 63: 79–85.
Barnes (1990) Proc. Natl. Acad. Sci, USA 87: 9183–9187.
Hofte, et al. (Jun. 1989) Microbiological Reviews 53 (2): 242–255.

*Primary Examiner*—Lynette R. F. Smith
*Assistant Examiner*—Amy J. Nelson
*Attorney, Agent, or Firm*—Ian C. McLeod

[57] ABSTRACT

Lepidopteran insect resistant transformed potato plants are described. In particular, the transformation of potato plants with five to ten copies of a translational fusion encoding the 68 kD lepidopteran-specific toxin from *Bacillus thuringiensis* var. kurstaki HD-73 and neomycin phosphotransferase II is described. The transgenic potato plants were resistant to the tobacco hornworm, a lepidopteran insect which is susceptible to *Bacillus thuringiensis* var. kurstaki toxin.

18 Claims, 9 Drawing Sheets

```
AGGCTTTAGTAGTAATAGTAGTGTAAGTATATAATAAGAGCTCCTATGTTCTCTTGGATACATCGTAGTGCTGAATTTAATATATAATTGCATCGGATAGTATT  1800
----+----|----+----|----+----|----+----|----+----|----+----|----+----|----+----|----+----|----+----|
 rGlyPheSerAsnSerSerValSerIleIleArgAlaProMetPheSerTrpIleHisArgSerAlaGluPheAsnAsnIleIleAlaSerAspSerIle

ACTCAAATCCCTGCAGTGAAGGGAAACTTTCTTTTTAATGGTTCTGTAATTCAGGACCAGGATTTACTGGTGGGGACTTAGTTAGATTAAATAGTAGTG  1900
----+----|----+----|----+----|----+----|----+----|----+----|----+----|----+----|----+----|----+----|
 ThrGlnIleProAlaValLysGlyAsnPheLeuPheAsnGlySerValIleSerGlyPheThrGlyGlyAspLeuValArgLeuAsnSerSerG

GAAATAACATTCAGAATAGAGGGTATATTGAAGTTCCAATTCACTTCCCATCGACATCTACCAGATATCGAGTTCGTGTACGGTATGCTTCTGTAACCCC  2000
----+----|----+----|----+----|----+----|----+----|----+----|----+----|----+----|----+----|----+----|
 lyAsnAsnIleGlnAsnArgGlyTyrIleGluValProIleHisPheProSerThrSerThrArgTyrArgValArgTyrAlaSerValThrPr

GATTCACCTCAACGTTAATTGGGTAATTCATCCATTTTTTCCAATACAGTACCAGCTACGTCATTAGATAATCTACAATCAAGTGATTTGGT  2100
----+----|----+----|----+----|----+----|----+----|----+----|----+----|----+----|----+----|----+----|
 oIleHisLeuAsnValAsnTrpGlyAsnSerSerIlePheSerAsnThrValProAlaThrSerLeuAspAsnLeuGlnSerSerAspPheGly

TATTTTGAAAGTGCCAATGCTTTTACATCTTCATTAGGTAATATAGTAGGTGTTAGAAATTTTAGTGGGACTGCAGGAGTGATAATAGACAGATTTGAAT  2200
----+----|----+----|----+----|----+----|----+----|----+----|----+----|----+----|----+----|----+----|
 TyrPheGluSerAlaAsnAlaPheThrSerLeuGlyAsnIleValGlyValArgAsnPheSerGlyThrAlaGlyValIleIleAspArgPheGluP

TTATTCCAGTTACTGCAACACTC  2300
----+----|----+----|---
 heIleProValThrAlaThrLeu
```

LEPIDOPTERAN INSECT RESISTANT TRANSGENIC POTATO PLANTS

BACKGROUND OF THE INVENTION

(1) Field of the Invention

The present invention relates to transgenic potato plants (*Solanum tuberosum*) which are lepidopteran insect resistant. In particular, the present invention relates to potato plants containing multiple repeating segments of DNA which encode an endotoxin from *Bacillus thuringiensis* so that the potato plant is provided with the insect resistance.

(2) Prior Art

It is well known that the bacterium *Bacillus thuringiensis* (B.t.) produces proteinaceous parasporal inclusions during sporulation. These *Bacillus thuringiensis* proteins are toxic and highly specific to certain lepidopteran, coleopteran, and dipteran insects (Hofte, H. and H. R. Whiteley, Microbiological Reviews, 53, 242–255 (1989)). Crystal and spore preparations from *B. thuringiensis* var. kurstaki (B.t.k.) have been used for many years as insecticides to control a variety of lepidopteran insects (Dulmage, H. T., Microbial Control of Pest and Plant Diseases 1970–1980 in: H. D. Burges (ed), Academic, London, pp. 193–222 (1980)). The protoxin from *Bacillus thuringiensis* var. kurstaki has a size of 130 kD, which is converted to a biologically active polypeptide of 68 kD in the midgut of susceptible insects (Bulla, L. A., Jr., et al., Biochem. Bio Phys. Res. Commun. 91, 1123–1130 (1979); and Adang, M. J., et al., Gene, 36, 289–300 (1985)).

Because *Bacillus thuringiensis* proteins have short half-lives when applied topically (Beegle, C. C., et al., Environ. Entomol., 10, 400–401 (1981)), introduction of *Bacillus thuringiensis* genes into plants could be a better utilization of this biological pest control system. Transgenic tobacco, tomato, and cotton plants containing *Bacillus thuringiensis* var. kurstaki genes have been reported to be resistant to attacks from target lepidopteran insects (Perlak, F. J., et al., Bio/technology 8, 939–943 (1990); Barton, K. A., et al., Plant Physiol. 85, 1103–1109 (1987); Vaeck, M., et al., Nature, 328, 33–37 (1987); and Delannay, X., et al., Bio/Technology, 7, 1265–1269 (1989)). Hornworm has been found to be susceptible to the *Bacillus thuringiensis* var. kurstaki encoded toxin in tobacco (MacIntosh, S. C., et al., J. Invertebrate Pathology, 56, 258–266 (1990)).

The problem is to provide the DNA encoding the protein in potatoes such that a sufficient amount is encoded in the plant to make it resistant to the lepidopteran insects. This has not been accomplished by the prior art.

SUMMARY OF THE INVENTION

It is therefore an object of the present invention to provide novel transgenic potato plant which are resistant to Lepidopteran insects. It is further an object of the present invention to provide the transgenic plants which contain multiple repeating tandem segments of *Bacillus thuringiensis* DNA encoding an endotoxin or endotoxins. These and other objects will become increasingly apparent by reference to the following description and the drawings.

BRIEF DESCRIPTION OF THE DRAWINGS

FIGS. 1A–1 to 1A–3 show the DNA sequence of the B.t.k. gene in pWB139 encoding the truncated endotoxin.

DETAILED DESCRIPTION OF THE INVENTION

The present invention relates to a transformed potato plant containing DNA encoding a *Bacillus thuringiensis* end Materials and Method
Plasmid The binary plasmid pWB139 was obtained from Dr. W. M. Barnes of Washington University, St. Louis, Mo. It contains a translational fusion encoding the 68 kD *Bacillus thuringiensis* toxin from *Bacillus thuringiensis* var. kurstaki HD-73 (Adang, M. J., et al., Gene, 36, 289–300 (1985)) and neomycin phosphotransferase II from the *E. coli* transposon Tn5 as shown in FIG. 1. This fused gene is regulated by the cauliflower mosaic virus 35S promoter and the 3' region of the tomato proteinase inhibitor I (Tom PI 3') gene. This cassette is further flanked by the nopaline synthase (NOS) promoter and terminator. This plasmid is based on the broad host-range vector pRK252 (Ditta, G., et al., Plasmid, 13, 149–153 (1985)) and is identical to pWB146 (Barnes, W. M., Proc. Natl. Acad. Sci. USA, 87, 9183–9187 (1990)), except that the *Bacillus thuringiensis* var. kurstaki endotoxin codons 1 through 612 replace the firefly luciferase codons of pWB146. In pWB139, only codons 1–612 from the full length btkgene are used. The reason for not using the full length btk codons is that the amino terminal 68 kD of the peptide has previously been shown to be sufficient for biological activity (Adang, M. J., et al., Gene 36, 289–300 (1985)). The nucleotides encoding the bt protein in pWB139 are shown in FIGS. 1A–1 to 1A–3 in the region between 387 to 2233 as disclosed above.

Transformation, Regeneration, and Selection

Leaf sections (15 mm in width) from potato selection FL1607 (obtained as axenically-grown plantlets) were inoculated with a ten-fold dilution of an overnight culture of *Agrobacterium tumefaciens* strain Wag11 containing pWB139, following procedures previously described (Horsch, R. B., et al., Plant Molecular Biology Manual, Kluwer Academic Publishers, Dordrecht, pp. A5:1–9 (1989)). This potato plant has a high transformation rate with *Agrobacterium tumefaciens* and thus is easier to use than other plants. The media used for shoot regeneration were from Wenzler et al (Wenzler, H., et al., Plant Science, 63, 79–85 (1989)), except that stage II medium contained 250 mg/l augmentin (Beecham Laboratories, Bristol, Tenn.). Regenerated shoots were transferred to Murashige and Skoog (MS) medium (Murashige, T., et al., Physiol. Plant., 15, 473–497 (1962)) supplemented with 50 mg/l kanamycin for selection. Cultures were maintained in a tissue culture room at 22±2° C. under a light intensity of 60$\mu$E $m^{-2}$ $sec^{-1}$ and a photoperiod of 16 hr/day provided by cool white fluorescent light.

Screening of Putative Transformants Using PCR

The PCR was performed using a DNA Thermal Cycler (Perkin Elmer Cetus) for 30 cycles of 2 minutes at 95° C., 2 minutes at 65° C., and 5 minutes at 72° C. The PCR reaction included 20 mM Tris buffer (pH 8.55), 2.5 mM $MgCl_2$, 16 mM $(NH_4)_2SO_4$, and 0.15 mg/ml bovine serum albumin (BSA), 0.2 mM dNPT's, 5 units Taq polymerase (Biotechnology Systems, New England Research Products, Boston, Mass.), 20 pM of each of the primers (WB241 and WB242), and 0.25 $\mu$g sample DNA in a reaction volume of 100 $\mu$l. The primers WB241 and WB242 have 100% homology to their target templates and amplify a 1090 base pair region of the btk:npt construct. The primers WB241 and WB242 are 30 and 32 base pairs in length, respectively. Their nucleotide sequences are 5'-TGATCTGGACGAAGAGCATCAGGGGCTCGC (WB241) and 5'-TATTGCCAAATGTTTGAAC (WB242).

The amplified DNA was subjected to electrophoresis in a 1% (w/v) agarose gel at 5 v/cm for 1.5 hours and blotted into a Nytran membrane using capillary transfer in 10× sodium chloride 0.18 M; sodium phosphate; 0.01M ethylene diamine tetramine (EDTA) 0.001M (SSPE) (Sambrook, J., et al., Molecular Cloning: A Laboratory Manual, second edition, Cold Spring Harbor Laboratory Press, Cold Spring Harbor (1988). Hybridization was performed following a modification of Southern's procedure (Southern, E. M., J. Mol. Biol. 98, 503–517 (1975)) provided by Schleicher & Schuell, Inc. (Publication No. 77). In this procedure, the membrane containing immobilized DNA was treated for two hours in a pre-hybridization solution containing 6× SSPE, 0.5% (w/v) sodium dodecyl sulfate (SDS), 0.2% (w /v) BSA, and 0.2% (w/v) ficol (MW 400,000). The membrane was then hybridized to a $^{32}$P-labeled 2.6 kb Hind III fragment of pWB139 which encodes the entire translational fusion. This fragment was labeled by random primed labeling (Feinberg, A. P., et al., Annu. Biochem., 132, 6–13 (1883)) using a kit from DuPont (Wilmington, Del.). Hybridization was performed inside a plastic bag containing a 25 ml solution of 6× SSPE, 0.5% (w/v) SDS, and approximately 5–20 ng/ml of the probe DNA and was carried out at 60° C. overnight. After hybridization, the membrane was washed twice in 6× SSPE and 0.5% (w/v) SDS at room temperature for 15 minutes, then twice in 1× SSPE and 0.5% (w/v) SDS at 37° C. for 15 minutes, and finally in 0.1× SSPE and 0.5% (w/v) SDS at 65° C. for 30 minutes. Autoradiography was performed using Kodak X-omat AR-5 film exposed at −70° C. for 2 hours with an intensifying screen (Lightning Plus; DuPont, Wilmington, Del.), and developed in an automatic film developer.

Confirmation of Gene Integration by Southern Blot Hybridization of Restricted DNA Total DNA was isolated from transformed and untransformed FL1607 potato plants as described (Rogers, S. O., et al., Extraction of DNA from plant tissues, in: S. B. Gelvin and R. A. Schilperoort (Eds), Plant Molecular Biology Manual, Kluwer Academic Publishers, Dordrecht, pp. A6: 1–11 (1989)). DNA (250 $\mu$g) from each plant was digested with 150 units of the restriction enzymes Bam HI or Hind III at 37° C. overnight. The digested DNA was subjected to electrophoresis in a 0.8% (w/v) agarose gel at 1.5 v/cm overnight. The procedures for Southern blot hybridization and autoradiography were the same as described earlier in the PCR analysis, except that the film was exposed for seven days at −70° C. For reconstruction studies pWB139 plasmid DNA (250, 1250, and 2500 pg, corresponding to 1, 5, and 10 copies of the translational fusion in 250 $\mu$g potato DNA) was digested with Bam HI and run parallel to the potato DNA.

Detection of the NPT II mRNA in the Transgenic Potato Plant

Fully expanded young leaves (10 g) were collected from transgenic and control potato and tobacco (provided by Dr. Wayne Barnes, Washington University, St. Louis, Mo. and used as positive control in mRNA purification and cDNA synthesis) plants. Because expression of the translational fusion in tobacco is partially regulated by the 3' terminator of tomato proteinase inhibitor I and is wound-enhanceable, the leaves were pricked with a scalpel and kept overnight in a covered 250 ml glass beaker lined with two pieces of moist filter paper. The following morning, the leaves were ground in liquid nitrogen and total RNA was extracted according to Gilmour et al (Gilmour, S. J., et al., Plant Physiol., 87, 745–750 (1988)). Poly A+ mRNA was purified using Hybond-mAP affinity paper (Wreschner, D. H., et al., Nucl. Acids Res. 12, 1349–1359 (1984)). First strand cDNA was synthesized in a 50 $\mu$l reaction buffer containing 50 mM Tris-HCl (pH 8.3), 75 mM KCl, 3 mM $MgCl_2$, 10 mM dithiothreitol, 50 $\mu$g/ml oligo $(dT)_{12-18}$, 500 $\mu$M each dATP, dGTP, dCTP, and dTTP, 2.5 μl (500 units) M-MLV reverse transcriptase (Bethesda Research Laboratory, Life Technologies, Inc.), and 5 μg purified poly A$^+$ mRNA sample. The reactions were incubated at 37° C. for one hour, then terminated by adding 1 μl of 0.25 M Na$_2$ EDTA (pH 7.5) and placed on ice. A 5 μl sample of the reaction was used as template in the subsequent PCR amplification. The conditions for the PCR were the same as described earlier, except that the pair of primers used (MB23 and MB24) amplify a different region (720 bp) of the btk:npt fusion. The primers MB23 and MB24 and 29 and 25 base pairs in length respectively. Their nucleotide sequences are 5'-GCTATGACTGGGCACAACAGACAATCGGC for MB23 and 5'-CTCGTCAAGAAGGCGATAGAAGGCG for MB24. Electrophoresis, Southern blot hybridization, and autoradiography were conducted using the same procedures described earlier for PCR analysis. To check DNA contamination in the mRNA preparations, parallel cDNA synthesis reaction and PCR were performed without reverse transcriptase.

Insect Assays

Bioassays were conducted on leaf disks (2 cm diameter) punched out from fully expanded young leaves of transformed and control potato plants in the morning in the greenhouse. The leaf disks were placed singly in moist, filter paper-lined, polystyrene petri dishes (50 ×9 mm, with snap-on lids) and brought to the laboratory. The initial area of each disk was measured on a portable leaf area meter (Model L1-3000, Lambda Instruments Corporation, USA). The following day, each leaf disk was infested with five healthy, neonate tobacco hornworm larvae. After 24 hours, larvae were removed from petri dishes and the area of each leaf disk was measured on the area meter. The difference between the initial and the final leaf areas represented the leaf area consumed and was used as an indicator of insect feeding. Since variations in thickness of potato leaves could mask feeding differences, the dry weight of insect frass was also used as a parameter of insect feeding. Insect frass collected from each petri dish was dried for 72 hours and weighed on a microbalance. Larval mortality, if any, was also recorded.

Insect feeding activity was measured on six leaf disks from the transformed potato plant and 33 leaf disks from the control potato plant. All feeding tests were conducted at 25° to 27° C., 65 to 75% relative humidity, and under a 12:12 hour (light:dark) photoperiod. Statistical differences between feeding activity on transformed and control leaf disks were computed by the General Linear Model procedure of Analysis of Variance and the means were compared by Tukey's test (Wilkinson, L., SYSTAT: The system for statistics, SYSTAT, Inc., Prints, Evanston, Ill., pp. 677 (1990)).

Results and discussion

In vitro shoot regeneration from leaf explants inoculated with Agrobacterium was efficient. Callus formed on the edges of leaf explants cultured on stage I medium two to three weeks following bacterial inoculation. After another four to six weeks on stage II medium, shoots were regenerated from the callus tissue. Two hundred and forty-three shoots were regenerated from fifty leaf explants. Twenty-four of these shoots were able to produce roots (3 to 9 mm in length) in the medium containing 50 mg/l kanamycin, while none of the 25 shoots from untransformed control plants produced roots when cultured in the same selection medium.

Figure 1:
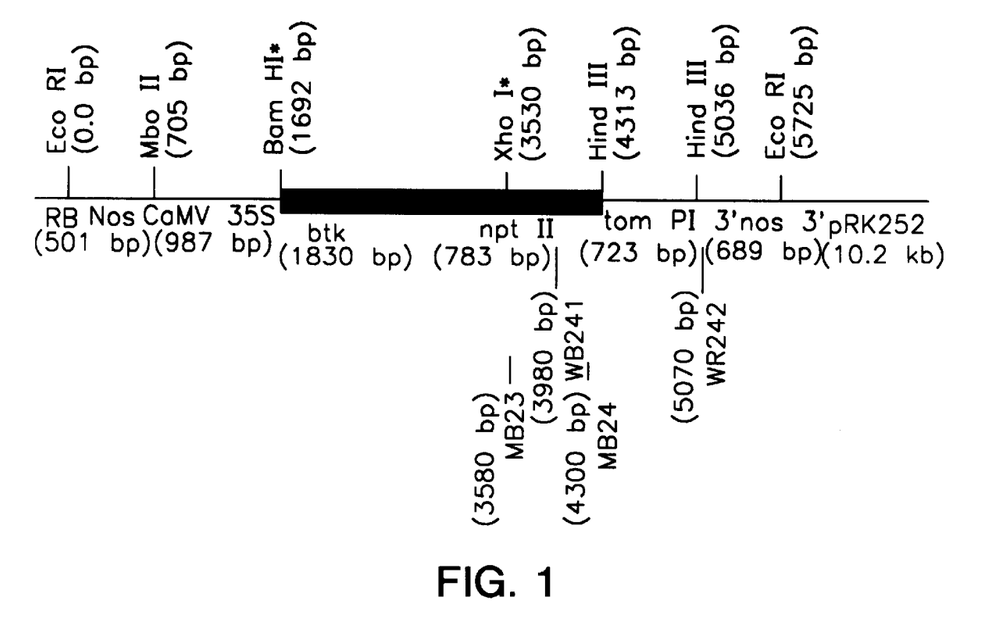
FIG. 1 is a diagram of the plasmid pWB139 where RB is right border of the T-DNA; Nos is the nopaline synthase promoter; CaMV 35S is the cauliflower mosaic virus 35S promoter; btk is the DNA sequences encoding the 68 kD B.t.k. toxin (only codons 1–612 from the full length gene were used); nptII is the DNA sequences encoding neomycin phosphotransferase II (in a frame translational fusion following the btk codons); tom PI 3' is the tomato proteinase inhibitor I transcription terminator; nos 3' is the nopaline synthase transcription terminator; * is the unique site in pWB139; WB241 and WB242 are primers used in PCR-amplified DNA and MB23 and MB24 are primers used in PCR-amplified cDNA. The distance between WB241 and WB242 is 1090 bp and between MB23 and MB24 is 720 bp. The left border of the T-DNA has been removed. The abbreviation "bp" is base pairs.
Figure 1A:
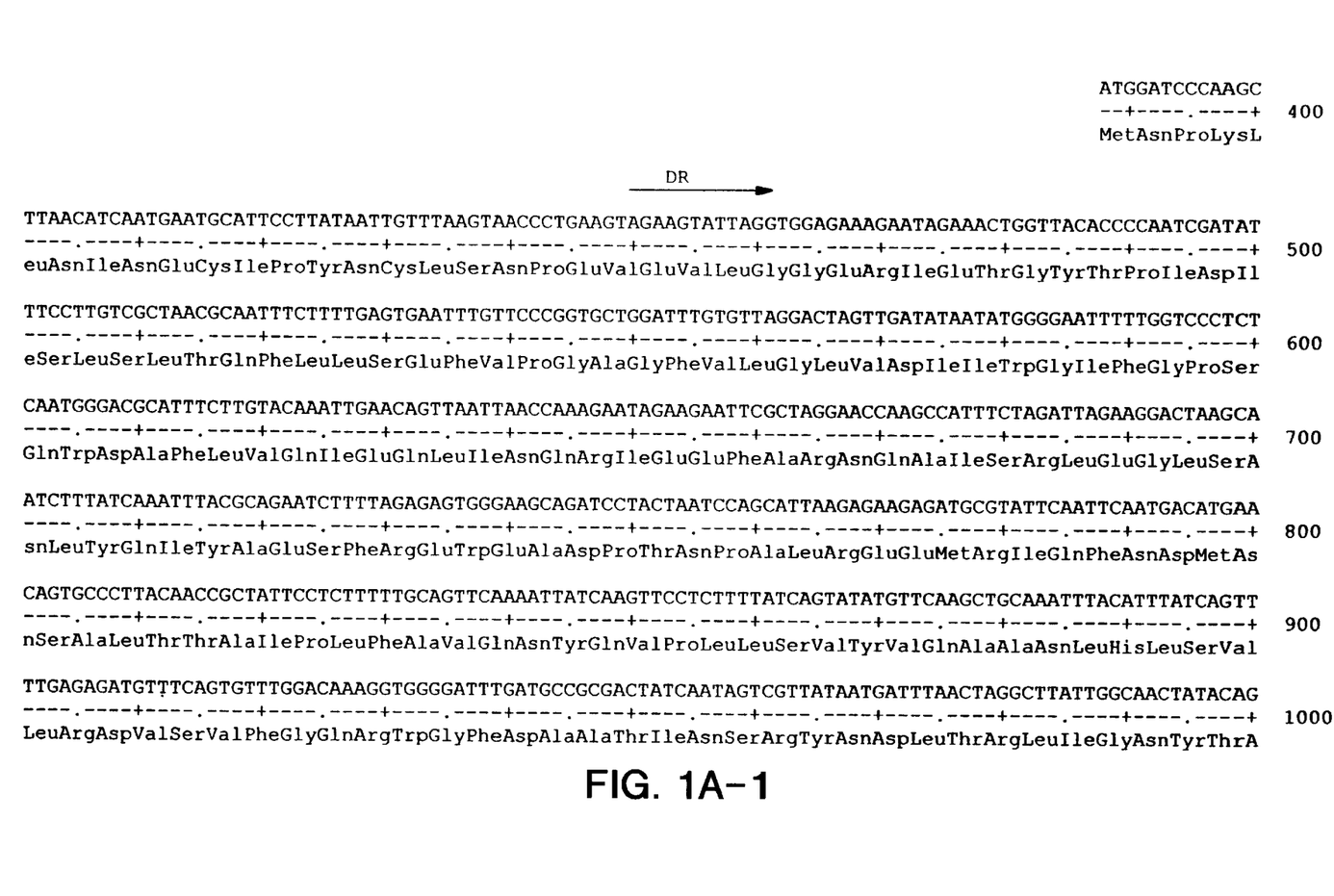
Figure 1A:
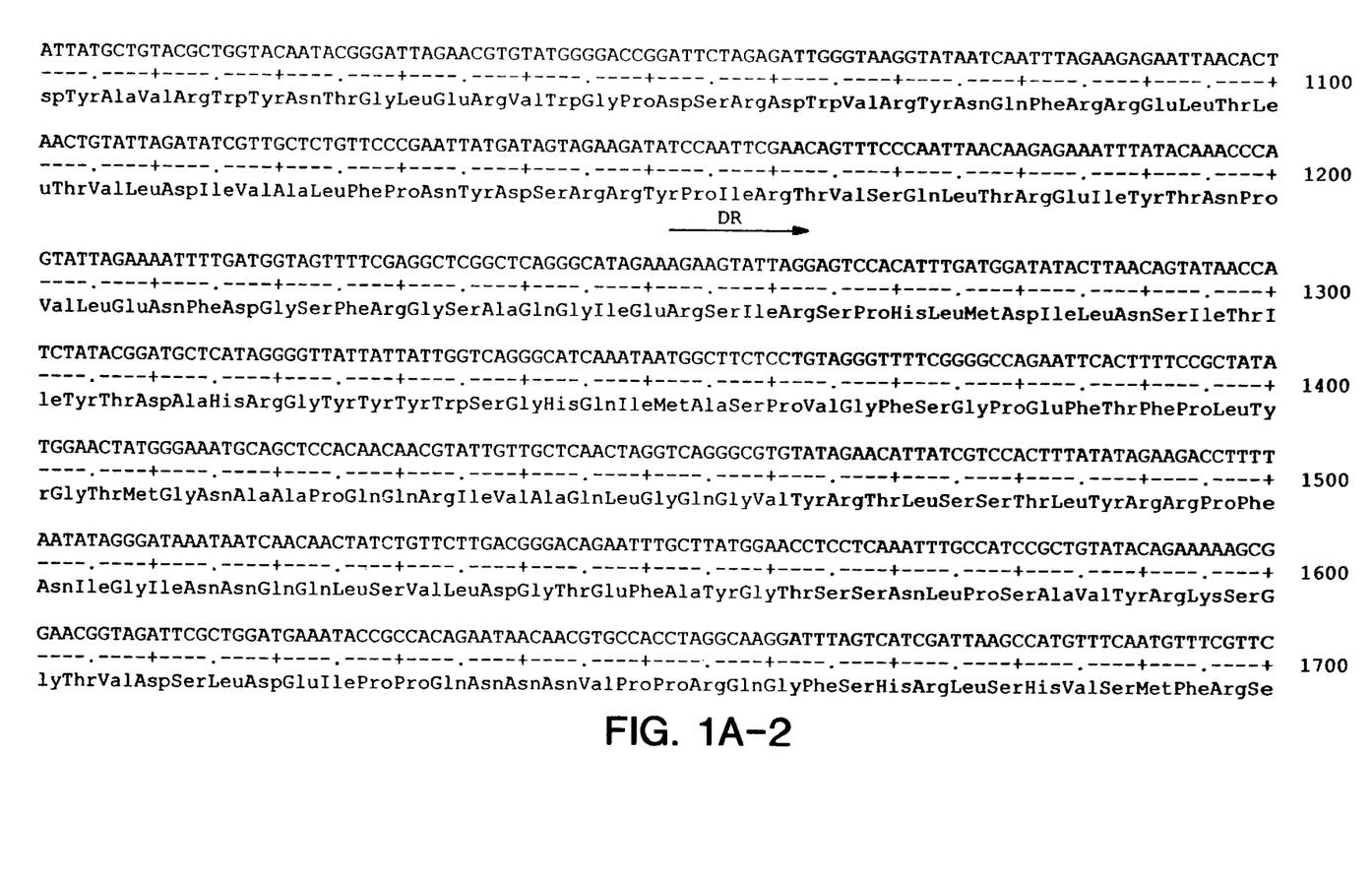
Figure 1A:
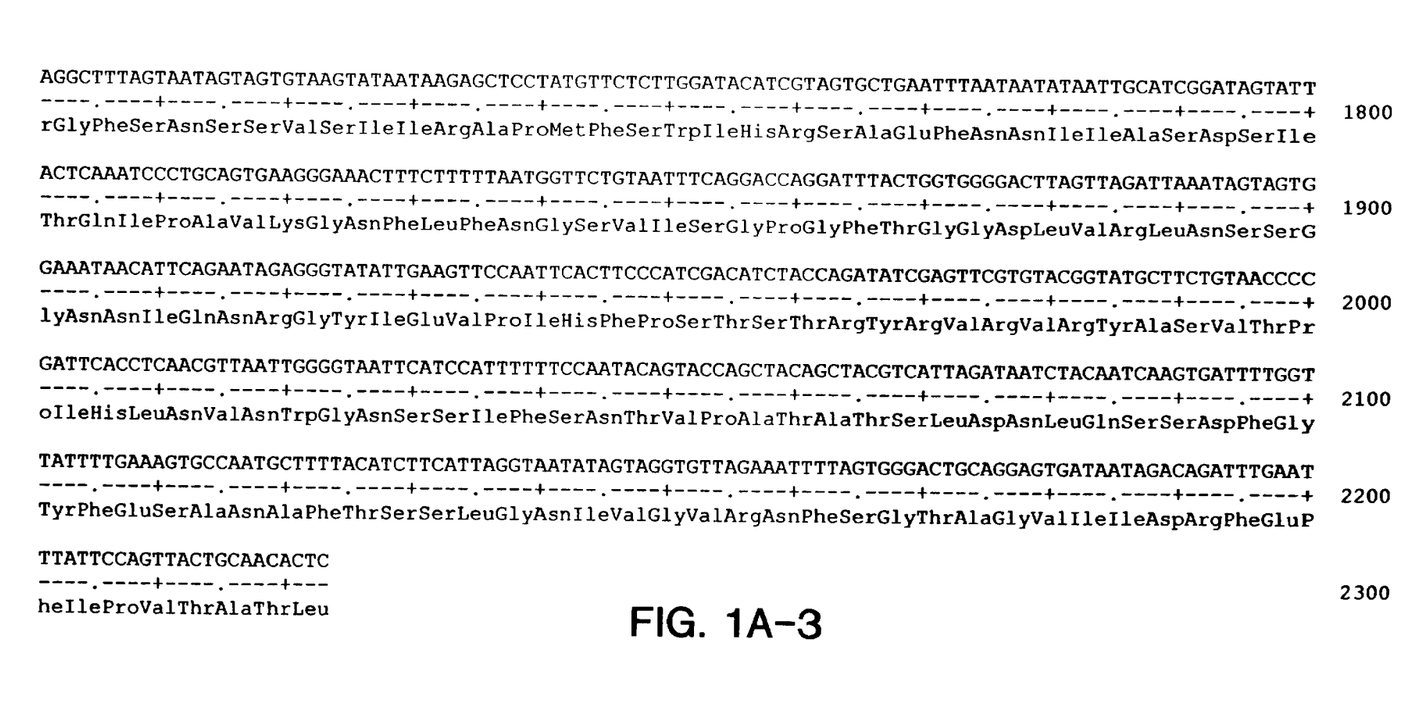
Figure 2:
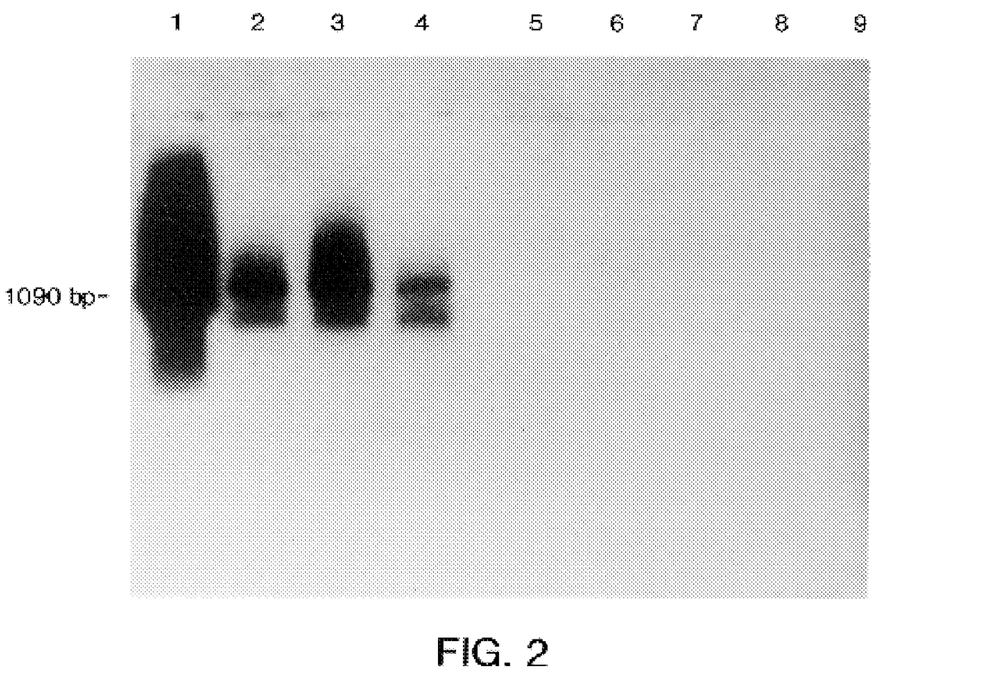
FIG. 2 is an autoradiogram of Southern blot of PCR amplified DNA from pWB139, untransformed FL1607, and seven regenerated potato plants capable of rooting in medium containing 50 mg/l kanamycin. PCR was performed using a pair of primers (WB241 and WB242) amplifying a 1090 bp region of the translational fusion. After PCR, the samples were subjected to electrophoresis in a 1% (w/v) agarose gel at 5 v/cm for 1.5 hours (DNA migration was from top down). Amplified DNA was blotted onto a Nytran membrane, and hybridized to a $^{32}$P-labeled 2.6 kb Hind III fragment of pWB139 covering the entire region of the translational fusion. BstE II digested lambda DNA was used as the size standard. Lane 1: DNA homologous to the probe was amplified using pWB139 DNA as the template; lane 2 to 4: DNA homologous to the probe was amplified using total DNA extracted from three regenerated FL1607 plants as the template; lane 5 to 8: DNA homologous to the probe was not amplified using DNA extracted from four regenerated FL1607 plants; lane 9: DNA homologous to the probe was not amplified using DNA from untransformed FL1607. bp=base pairs.
Figure 3:
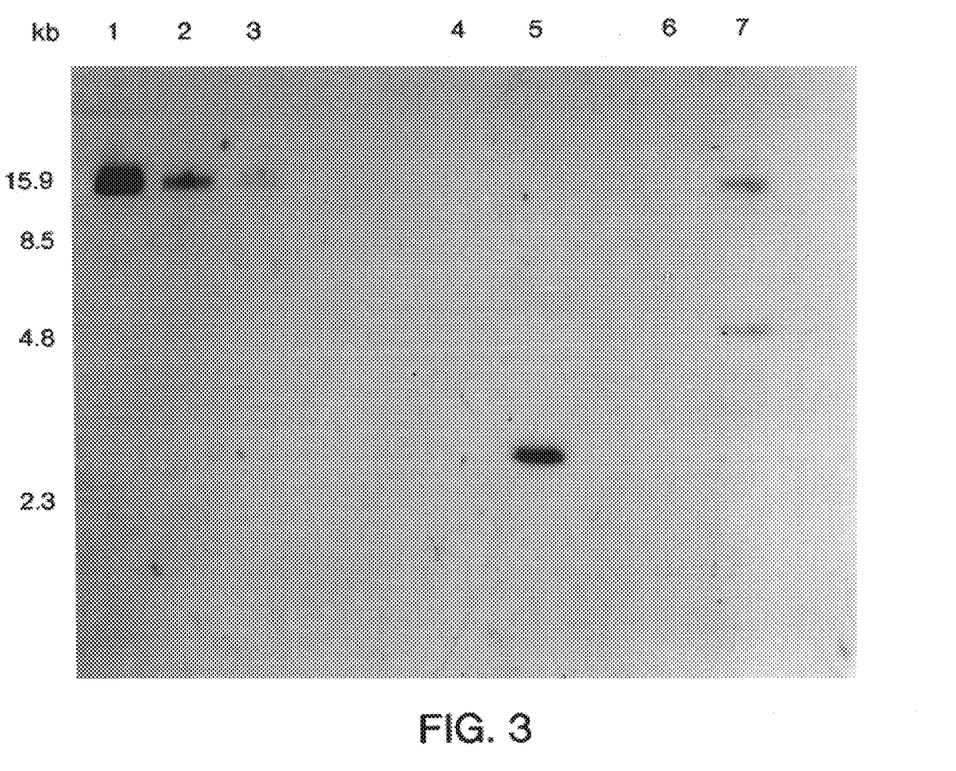
FIG. 3 is an autoradiogram of a Southern blot of pWB139, as well as total DNA from untransformed and transformed FL1607 plants. 250 μg of potato DNA was digested with 150 units restriction enzyme at 37° C. overnight. The digests were subjected to electrophoresis, transferred to a Nytran membrane, and hybridized to the $^{32}$P-labeled 2.6 Kb Hind III fragment of pWB139. DNA migration was from top down. BstE II-digested lambda DNA was used as the size standard. 250, 1250, and 2500 pg of pWB139 DNA corresponding to 1, 5, and 10 copies of the translational fusion in 250 μg potato DNA were used to estimate the copy number of the integrated btk:npt gene fusion. Lane 1: 2500 pg Bam HI-digested pWB139 DNA; lane 2: 1250 pg Bam HI-digested pWB139 DNA; lane 3: 250 pg Bam HI-digested pWB139 DNA; lane 4 and 5: Hind III-digested total DNA from untransformed and transformed FL1607, respectively; lane 6 and 7: Bam HI-digested total DNA from untransformed and transformed FL1607, respectively. kb=kilobase pairs.

The presence of the btk:npt gene fusion was detected by Southern blot hybridization of PCR amplified DNA from leaf samples in three of the seven selected plants (FIG. 2). Screening for transgenic plants by PCR is efficient, although a positive signal detected by PCR does not necessarily mean that the gene has been integrated into the plant genome. Based on the results of PCR analysis, three plants which were positive by PCR were further analyzed for integration of the gene into the plant genome. Southern blot hybridization of Hind III digested total DNA from one of these plants, revealed a 2.6 kb band (FIG. 3), confirming the results of PCR that the btk:neo fusion was present in the plant genome. There were two bands (5 and 14 kb each) demonstrated in the Bam HI digestion. Because Bam HI recognizes a unique site in the plasmid pWB139, this result suggests at least two independent integration events. Results of the reconstruction analysis indicate that five to ten copies of the gene fusion are integrated, possibly in a tandem fashion. Therefore, it is concluded that the btk:npt translational fusion has been integrated into the genome of this plant without any major structural alterations within the translational fusion. However, two of the three plants which were positive by PCR did not display any positive signal by genomic Southern analysis (data not shown). The discrepancy between PCR and Southern blot of the restricted genomic DNA may be due to a very low proportion of cells being transformed.

Figure 4:
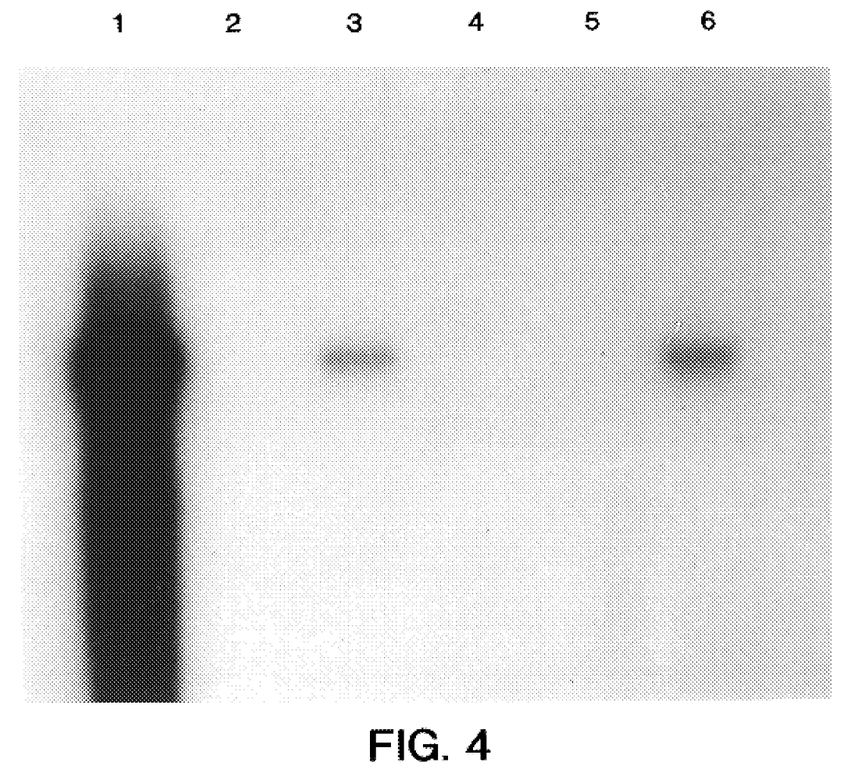
FIG. 4 is an autoradiogram of Southern blot of PCR-amplified cDNA homologous to the translational fusion in transgenic FL1607 and tobacco plants. cDNA was synthesized from purified poly A+ mRNA, then PCR-amplified using a pair of primers (MB23 and MB24) which amplify a 720 bp region of the translational fusion. Amplified DNA was subjected to electrophoresis in a 1% (w/v) agarose gel, blotted onto a Nytran membrane, and hybridized to a $^{32}$P-labeled 2.6 kb Hind III fragment of pWB139. DNA migration was from top down and BstE II digested lambda DNA was used as the size standard. DNA contamination in mRNA preparations was checked by parallel cDNA synthesis and PCR without reverse transcriptase. Lane 1: PCR-amplified DNA homologous to the probe using pWB139 DNA as the template; Lane 2: DNA homologous to the probe was not amplified from transgenic tobacco when cDNA synthesis was performed without reverse transcriptase; lane 3: PCR-amplified DNA homologous to the probe using cDNA from transgenic tobacco as the template; lane 4: DNA homologous to the probe was not amplified using cDNA from untransformed FL1607 as the template; lane 5: DNA homologous to the probe was not amplified from transgenic FL1607 when cDNA synthesis was performed without reverse transcriptase; lane 6: PCR-amplified DNA homologous to the probe using cDNA from transgenic FL1607 as the template.

Expression of the translational fusion in the transgenic potato plant was detected by Southern blot hybridization of PCR amplified cDNA synthesized from purified mRNA of the transgenic potato plant (FIG. 4). The possibility of DNA contamination was ruled out by the fact that no DNA was detected after PCR amplification without adding reverse transcriptase to the reaction.

Figure 5:
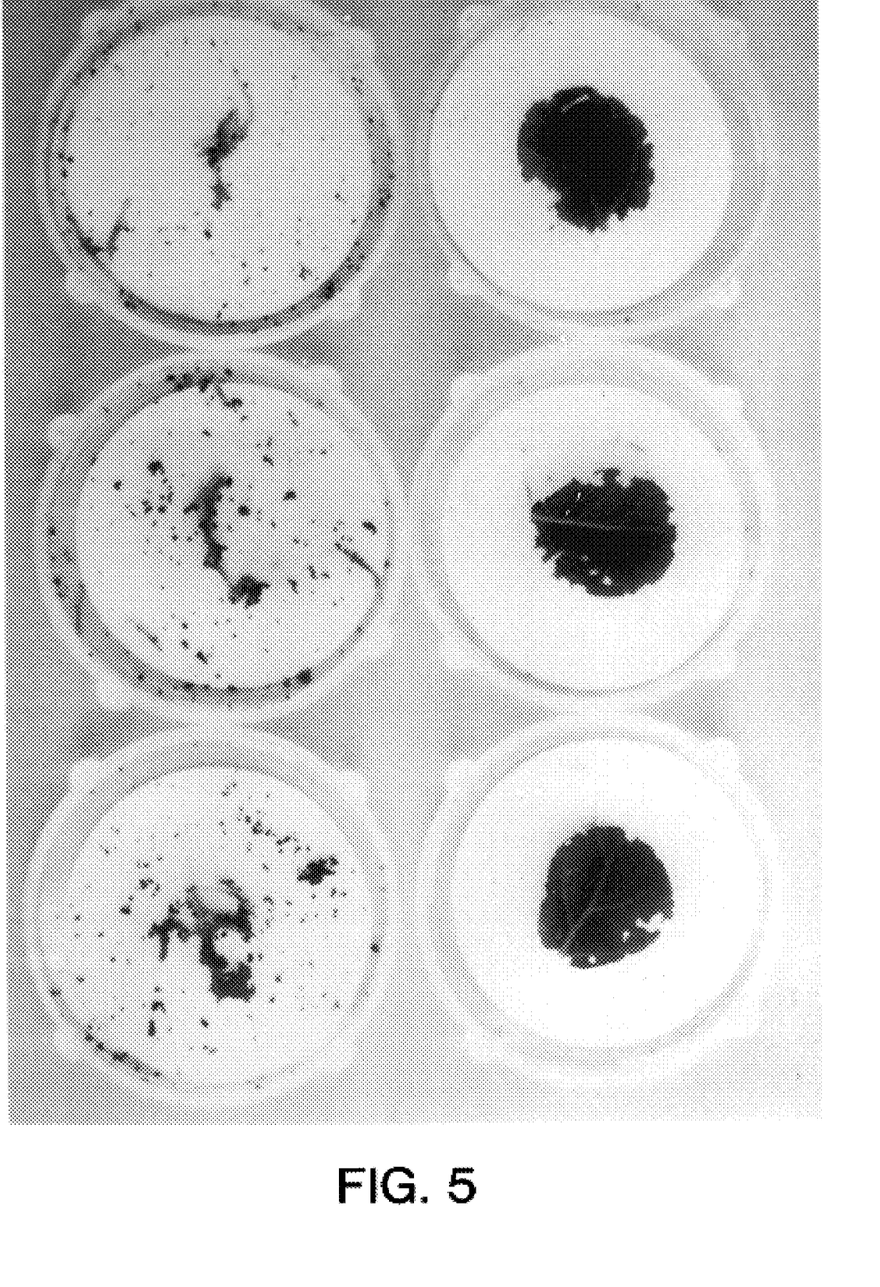
FIG. 5 is leaf area consumption by tobacco hornworm (*Manduca sexta*) in a petri dish (5 cm diameter) after 24 hours in laboratory tests. Left row: leaf disks (2 cm diameter) taken from an untransformed FL1607 plant; right row; leaf disks (2 cm diameter) taken from the transformed FL1607 plant.
Figure 6:
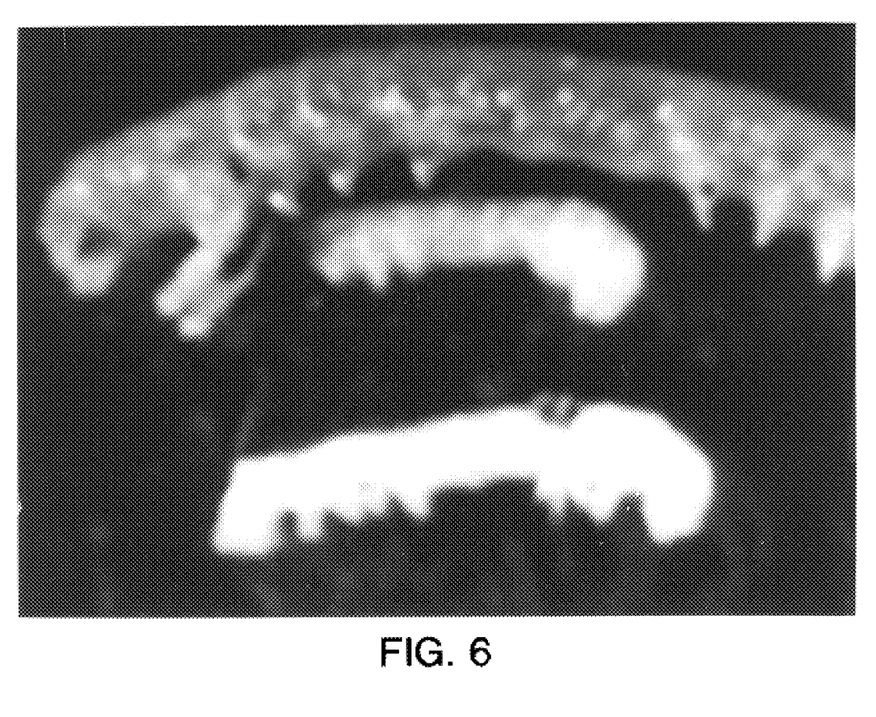
FIG. 6 is a photograph showing the growth of first instar larvae of hookworm over 24 hours. The upper insect was fed on control leaf disc and the lower two (2) insects were fed on the transgenic potato leaf discs for 24 hours. The lower two (2) larvae are stunted.

Insect feeding differed distinctly between leaf disks of transformed and control plants as shown in FIG. 5. The neonate tobacco hornworm larvae consumed significantly more leaf area on leaf disks from the control potato plant than on leaf disks taken from the transformed potato (Table I). Also, frass collected from petri dishes containing transgenic potato leaf disks weighed significantly less than that collected from dishes containing the control leaves (Table I). This difference also indicates reduced feeding on the transformed potato plant. Although few neonates died after 24 hour confinement in the petri dishes, those that fed on leaf disks of the transformed potato plant were smaller, sluggish, and pale, compared with those that fed on the control leaf disks (FIG. 5). FIG. 6 shows the relative size of the hookworms for a control (upper) and transgenic plant feedings (two lower). Thus, transformed potato plant foliage was relatively more resistant to tobacco hornworm feeding.

TABLE I

Mean leaf area consumed by five neonate tobacco hornworm larvae in 24 hours and mean dry weight of frass on leaf disks of transformed and untransformed FL1607 plants.[a,b]

| Plant | Leaf area (cm$^2$ ± SD) | Frass weight (μg ± SD) |
| --- | --- | --- |
| Transformed | 0.61 ± 0.205 | 0.82 ± 0.404 |
| Untransformed | 1.86 ± 0.373 | 2.89 ± 0.769 |

[a]Means of six replications of transformed and 33 replications of control potato leaf disks;
[b]Means of transformed and untransformed in a column are significantly different (p < 0.001) using Tukey's procedure.

Expression of full-length bt genes in transgenic plants has been reported to be extremely low (Hofte, H. and H. R. Whiteley, Microbiological Reviews, 53, 242–255 (1989); and Vaeck, M., et al., Nature, 328, 33–37 (1987)). We also found low bt-expression in the transgenic potato plant and were unable to detect bt mRNA with Northern blot hybridization, although the bt gene used is truncated and a biologically active portion of the full length toxin (Adang, M. J., et al., Gene, 36, 289–300 (1985)). However, using PCR amplification of cDNA from reverse transcribed mRNA, we detected the expression of the btk:neo translational fusion in the transgenic potato plant.

It has been reported that degrees of insect resistance of transgenic plants are positively correlated with bt mRNA levels in the transgenic plants (Vaeck, M., et al., Nature, 328, 33–37 (1987)) and that transgenic tobacco and tomato plants with low btk gene expression still have substantial tolerance to the tobacco hornworm and other target insects (Vaeck, M., et al., Nature, 328, 33–37 (1987); and Delannay, X., et al., Bio/Technology, 7, 1265–1269 (1989)). In the present case, higher expression produces better results. The insect resistance of the transgenic potato plant demonstrated in the potato plants is particularly useful in reducing the amount of synthetic pesticides used in protecting potato crops worldwide.

The transgenic potato plant and seed potatoes are on deposit from Michigan State University, East Lansing, Mich. as a depository.

It is intended that the foregoing description be only illustrative of the present invention and that the present invention be limited only by the hereinafter appended claims.

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 1836
      (B) TYPE: Nucleic Acid
      (C) STRANDEDNESS: Single
      (D) TOPOLOGY: Linear    (ii) MOLECULE TYPE: Plasmid DNA    (iii) HYPOTHETICAL: No    (iv) ANTI-SENSE: No    (v) FRAGMENT TYPE: N-terminal, internal and C-terminal
      fragments    (vi) ORIGINAL SOURCE:
      (A) ORGANISM: Bacillus thuringiensis
      (B) STRAIN: N/A
      (C) INDIVIDUAL ISOLATE: pWB139
      (D) DEVELOPMENTAL STAGE: N/A
      (E) HAPLOTYPE: N/A
      (F) TISSUE TYPE: N/A
      (G) CELL TYPE: N/A
      (H) CELL LINE: N/A
      (I) ORGANELLE: N/A    (vii) IMMEDIATE SOURCE: N/A    (viii) POSITION IN GENOME: N/A    (ix) FEATURE:
      (A) NAME/KEY: endotoxin encoding DNA
      (B) LOCATION: BAM III to XhoI
         DNA fragment in pB139
      (C) IDENTIFICATION METHOD: sequencing
      (D) OTHER INFORMATION: DNA needed for endotoxin
         expression.

(x) PUBLICATION INFORMATION: Barnes, W. M., Proc. Natl. Acad. Sci.
      US, 87, 9183-9187 (1990)

(xi) SEQUENCE DESCRIPTION: SEQ ID NO:1:

```
                                                       ATGGATCCCA     10
                                                       MetAsnProL

AGCTTAACAT CAATGAATGC ATTCCTTATA ATTGTTTAAG TAACCCTGAA GTAGAAGTAT     70
ysLeuAsnIl eAsnGluCys IleProTyrA snCysLeuSe rAsnProGlu ValGluValL
    5          10          15          20          25

TAGGTGGAGA AAGAATAGAA ACTGGTTACA CCCCAATCGA TATTTCCTTG TCGCTAACGC    130
euGlyGlyGl uArgIleGlu ThrGlyTyrT hrProIleAs pIleSerLeu SerLeuThrG
    30          35          40          45

AATTTCTTTT GAGTGAATTT GTTCCCGGTG CTGGATTTGT GTTAGGACTA GTTGATATAA    190
lnPheLeuLe uSerGluPhe ValProGlyA laGlyPheVa lLeuGlyLeu ValAspIleI
```

|  | 50 | 55 | 60 | 65 |  |
|---|---|---|---|---|---|
| TATGGGAAT | TTTTGGTCCC | TCTCAATGGG | ACGCATTTCT | TGTACAAATT | GAACAGTTAA | 250 |
| leTrpGlyIl | ePheGlyPro | SerGlnTrpA | spAlaPheLe | uValGlnIle | GluGlnLeuI |  |
|  | 70 |  | 75 | 80 | 85 |  |
| TTAACCAAAG | AATAGAAGAA | TTCGCTAGGA | ACCAAGCCAT | TTCTAGATTA | GAAGGACTAA | 310 |
| leAsnGlnAr | gIleGluGlu | PheAlaArgT | snGlnAlaIl | eSerArgLeu | GluGlyLeuS |  |
|  | 90 | 95 | 100 | 105 |  |
| GCAATCTTTA | TCAAATTTAC | GCAGAATCTT | TTAGAGAGTG | GGAAGCAGAT | CCTACTAATC | 370 |
| erAsnLeuTy | rGlnIleTyr | AlaGluSerP | heArgGluTr | pGluAlaAsp | ProThrAsnP |  |
|  | 110 | 115 | 120 | 125 |  |
| CAGCATTAAG | AGAAGAGATG | CGTATTCAAT | TCAATGACAT | GAACAGTGCC | CTTACAACCG | 430 |
| roAlaLeuAr | gGluGluMet | ArgIleGlnP | heAsnAspMe | tAsnSerAla | LeuThrThrA |  |
|  | 130 | 135 | 140 | 145 |  |
| CTATTCCTCT | TTTTGCAGTT | CAAAATTATC | AAGTTCCTCT | TTTATCAGTA | TATGTTCAAG | 490 |
| laIleProLe | uPheAlaVal | GlnAsnTyrG | lnValProLe | uLeuSerVal | TyrValGlnA |  |
|  | 150 | 155 | 160 | 165 |  |
| CTGCAAATTT | ACATTTATCA | GTTTTGAGAG | ATGTTTCAGT | GTTTGGACAA | AGGTGGGGAT | 550 |
| laAlaAsnLe | uHisLeuSer | ValLeuArgA | spValSerVa | lPheGlyGln | ArgTrpGlyP |  |
|  | 170 | 175 | 180 | 185 |  |
| TTGATGCCGC | GACTATCAAT | AGTCGTTATA | ATGATTTAAC | TAGGCTTATT | GGCAACTATA | 610 |
| heAspAlaAl | aThrIleAsn | SerArgTyrA | snAspLeuTh | rArgLeuIle | GlyAsnTyrT |  |
|  | 190 | 195 | 200 | 205 |  |
| CAGATTATGC | TGTACGCTGG | TACAATACGG | GATTAGAACG | TGTATGGGGA | CCGGATTCTA | 670 |
| hrAspTyrAl | aValArgTrp | TyrAsnThrG | lyLeuGluAr | gValTrpGly | ProAspSerA |  |
|  | 210 | 215 | 220 | 225 |  |
| GAGATTGGGT | AAGGTATAAT | CAATTTAGAA | GAGAATTAAC | ACTAACTGTA | TTAGATATCG | 730 |
| rgAspTrpVa | lArgTyrAsn | GlnPheArgA | rgGluLeuTh | rLeuThrVal | LeuAspIleV |  |
|  | 230 | 235 | 240 | 245 |  |
| TTGCTCTGTT | CCCGAATTAT | GATAGTAGAA | GATATCCAAT | TCGAACAGTT | TCCCAATTAA | 790 |
| alAlaLeuPh | eProAsnTyr | AspSerArgA | rgTyrProIl | eArgThrVal | SerGlnLeuT |  |
|  | 250 | 255 | 260 | 265 |  |
| CAAGAGAAAT | TTATACAAAC | CCAGTATTAG | AAAATTTTGA | TGGTAGTTTT | CGAGGCTCGG | 850 |
| hrArgGluIl | eTyrThrAsn | ProValLeuG | luAsnPheAs | pGlySerPhe | ArgGlySerA |  |
|  | 270 | 275 | 280 | 285 |  |
| CTCAGGGCAT | AGAAGAAGT | ATTAGGAGTC | CACATTTGAT | GGATATACTT | AACAGTATAA | 910 |
| laGlnGlyIl | eGluArgSer | IleArgSerP | roHisLeuMe | tAspIleLeu | AsnSerIleT |  |
|  | 290 | 295 | 300 | 305 |  |
| CCATCTATAC | GGATGCTCAT | AGGGGTTATT | ATTATTGGTC | AGGGCATCAA | ATAATGGCTT | 970 |
| hrIleTyrTh | rAspAlaHis | ArgGlyTyrT | yrTyrTrpSe | rGlyHisGln | IleMetAlaS |  |
|  | 310 | 315 | 320 | 325 |  |
| CTCCTGTAGG | GTTTTCGGGG | CCAGAATTCA | CTTTTCCGCT | ATATGAACT | ATGGGAAATG | 1030 |
| erProValGl | yPheSerGly | ProGluPheT | hrPheProLe | uTyrGlyThr | MetGlyAsnA |  |
|  | 330 | 335 | 340 | 345 |  |
| CAGCTCCACA | ACAACGTATT | GTTGCTCAAC | TAGGTCAGGG | CGTGTATAGA | ACATTATCGT | 1090 |
| laAlaProGl | nGlnArgIle | ValAlaGlnL | euGlyGlnGl | yValTyrArg | ThrLeuSerS |  |
|  | 350 | 355 | 360 | 365 |  |
| CCACTTTATA | TAGAAGACCT | TTTAATATAG | GGATAAATAA | TCAACAACTA | TCTGTTCTTG | 1150 |
| erThrLeuTy | rArgArgPro | PheAsnIleG | lyIleAsnAs | nGlnGlnLeu | SerValLeuA |  |
|  | 370 | 375 | 380 | 385 |  |
| ACGGACAGA | ATTTGCTTAT | GGAACCTCCT | CAAATTTGCC | ATCCGCTGTA | TACAGAAAAA | 1210 |
| spGlyThrGl | uPheAlaThr | GlyThrSerS | erAsnLeuPr | oSerAlaVal | TyrArgLysS |  |
|  | 390 | 395 | 400 | 405 |  |
| GCGGAACGGT | AGATTCGCTG | GATGAAATAC | CGCCACAGAA | TAACAACGTG | CCACCTAGGC | 1270 |
| erGlyThrVa | lAspSerLeu | AspGluIleP | roProGlnAs | nAsnAsnVal | ProProArgG |  |
|  | 410 | 415 | 420 | 425 |  |
| AAGGATTAG | TCATCGATTA | AGCCATGTTT | CAATGTTTCG | TTCAGGCTTT | AGTAATAGTA | 1330 |
| lnGlyPheSe | rHisArgLeu | SerHisValS | erMetPheAr | gSerGlyPhe | SerAsnSerS |  |
|  | 430 | 435 | 440 |  |  |
| GTGTAAGTAT | AATAAGAGCT | CCTATGTTCT | CTTGGATACA | TCGTAGTGCT | GAATTTAATA | 1390 |

-continued

```
erValSerIl eIleArgAla ProMetPheS erTrpIleHi sArgSerAla GluPheAsnA
445             450             455             460

ATATAATTGC ATCGGATAGT ATTACTCAAA TCCCTGCAGT GAAGGGAAAC TTTCTTTTTA    1450
snIleIleAl aSerAspSer IleThrGlnI leProAlaVa lLysGlyAsn PheLeuPheA
465             470             475             480

ATGGTTCTGT AATTTCAGGA CCAGGATTTA CTGGTGGGGA CTTAGTTAGA TTAAATAGTA    1510
snGlySerVa lIleSerGly ProGlyPheT hrGlyGlyAs pLeuValArg LeuAsnSerS
485             490             495             500             505

GTGGAAATAA CATTCAGAAT AGAGGGTATA TTGAAGTTCC AATTCACTTC CCATCGACAT    1570
erGlyAsnAs nIleGlnAsn ArgGlyTyrI leGluValPr oIleHisPhe ProSerThrS
                510             515             520             525

CTACCAGATA TCGAGTTCGT GTACGGTATG CTTCTGTAAC CCCGATTCAC CTCAACGTTA    1630
erThrArgTy rArgValArg ValArgTyrA laSerValTh rProIleHis LeuAsnValA
                530             535             540             545

ATTGGGGTAA TTCATCCATT TTTTCCAATA CAGTACCAGC TACAGCTACG TCATTAGATA    1690
snTrpGlyAs nSerSerIle PheSerAsnT hrValProAl aThrAlaThr SerLeuAspA
                550             555             560             565

ATCTACAATC AAGTGATTTT GGTTATTTTG AAAGTGCCAA TGCTTTTACA TCTTCATTAG    1750
snLeuGlnSe rSerAspPhe GlyTyrPheG luSerAlaAs nAlaPheThr SerSerLeuG
                570             575             580             585

GTAATATAGT AGGTGTTAGA AATTTTAGTG GGACTGCAGG AGTGATAATA GACAGATTTG    1810
lyAsnIleVa lGlyValArg AsnPheSerG lyThrAlaGl yValIleIle AspArgPheG
                590             595             600             605

AATTTATTCC AGTTACTGCA ACACTC                                         1836
luPheIlePr oValThrAla ThrLeu
                610
```

We claim:

1. A transformed potato plant comprising DNA as set forth in SEQ ID NO:1 which encodes a *Bacillus thuringiensis* endotoxin, wherein five to ten copies of the DNA are integrated into the genome of the plant and wherein the endotoxin is expressed at a level such that the plant is resistant to Lepidopteran insects.

2. The transformed potato plant of claim 1 wherein the potato plant prior to transformation is *Solanum tuberosum* FL 1607.

3. The transformed potato plant of claim 1 wherein the DNA has been transformed into the plant using *Agrobacterium tumefaciens* as a vector.

4. The transformed potato plant of claim 1 wherein the DNA is linked to a marker DNA which allows selection for the transformed plant.

5. The transformed potato plant of claim 4 wherein the marker DNA encodes neomycin phosphotransferase II.

6. The transformed potato plant of claim 1 wherein the potato plant prior to transformation is *Solanum tuberosum* FL1607, wherein the DNA has been transformed into the plant using *Agrobacterium tumefaciens* as a vector, and wherein the DNA is linked to a marker DNA which allows selection for the transformed plant.

7. The transformed potato plant of claim 6 wherein the marker DNA encodes neomycin phosphotransferase II.

8. The transformed potato plant of claim 1 wherein the DNA is operably linked to a polyadenylation encoding DNA region.

9. The transformed potato plant of claim 8 wherein the polyadenylation encoding DNA region comprises Tom PI 3' and NOS 3'.

10. A method for producing a transformed potato plant which is resistant to Lepidopteran insects comprising:

(a) transforming potato plants with DNA encoding a *Bacillus thuringiensis* endotoxin as set forth in SEQ ID NO:1; and (b) selecting a transformed potato plant, wherein five to ten copies of the DNA are integrated into the genome of the plant and wherein the endotoxin is expressed at a level such that the plant is resistant to Lepidopteran insects.

11. The method of claim 10 wherein the transformed potato plant prior to transformation is *Solanum tuberosum* FL 1607.

12. The method of claim 10 wherein the DNA is transformed into the plant using *Agrobacterium tumefaciens* as a vector.

13. The method of claim 10 wherein the DNA is linked to a marker DNA which allows selection for the transformed plant.

14. The method of claim 13 wherein the marker DNA encodes neomycin phosphotransferase II.

15. The method of claim 10 wherein the transformed potato plant prior to transformation is *Solanum tuberosum* FL1607, wherein the DNA is transformed into the plant using *Agrobacterium tumefaciens* as a vector, and wherein the DNA is linked to a marker DNA which allows selection for the transformed plant.

16. The method of claim 15 wherein the marker DNA encodes neomycin phosphotransferase II.

17. The method of claim 10 wherein the DNA is operably linked to a polyadenylation encoding DNA region.

18. The method of claim 17 wherein the polyadenylation encoding DNA region comprises Tom PI 3' and NOS 3'.

* * * * *